United States Patent [19]

Fery et al.

[11] Patent Number: 5,052,219
[45] Date of Patent: Oct. 1, 1991

[54] PROCEDURE AND CELL FOR MEASURING COEFFICIENTS OF ADHESION AND FRICTION OF A DRILLING FLUID

[75] Inventors: Jean-Jacques Fery, Bar-le-Duc; Jean-Marc Patroni, Les Ulis, both of France

[73] Assignee: Total Compagnie Francaise des Petroles, Paris, France

[21] Appl. No.: 477,401

[22] Filed: Feb. 9, 1990

[30] Foreign Application Priority Data

Feb. 9, 1989 [FR] France .................. 89 01688

[51] Int. Cl.$^5$ .......................................... G01N 11/10
[52] U.S. Cl. ........................................ 73/153; 73/9; 73/60; 73/151
[58] Field of Search ................ 73/9, 58, 60, 61.4, 73/64.4, 81, 151, 153, 843, 866

[56] References Cited

U.S. PATENT DOCUMENTS

| | | | |
|---|---|---|---|
| 1,960,226 | 5/1934 | Schoenberg | 73/60 |
| 2,691,298 | 10/1954 | Cook | 73/61 |
| 2,752,778 | 7/1956 | Roberts et al. | 73/60 |
| 2,801,537 | 8/1957 | Kabelitz et al. | 73/58 |
| 4,173,142 | 11/1979 | Heinz | 73/60 |
| 4,458,528 | 7/1984 | Roper et al. | 73/151 |
| 4,557,142 | 12/1985 | Hensley et al. | 73/153 |
| 4,601,195 | 7/1986 | Garritano | 73/60 |

FOREIGN PATENT DOCUMENTS

| | | | |
|---|---|---|---|
| 0589365 | 1/1978 | U.S.S.R. | 73/153 |
| 1462167 | 2/1989 | U.S.S.R. | 73/866 |

OTHER PUBLICATIONS

World Oil, vol. 183, No. 1, Jul. 1976, pp. 105–110, S. E. Alford: "New Technique Evaluates Drilling Mud Lubricants".

Primary Examiner—Hezron E. Williams
Assistant Examiner—Craig Miller
Attorney, Agent, or Firm—Sughrue, Mion, Zinn, Macpeak and Seas

[57] ABSTRACT

The process for measuring the coefficients of adhesion and friction of a drilling fluid involves, following the standardized filtration of the drilling fluid or mud from which a solid phase "filtration cake" and a liquid phase or filtrate collected on the downstream side of a filter 15 are obtained, placing a metal piston skirt 29 in contact with a filtration cake in the presence of a contact pressure, and measuring the moments of adhesion and friction when the skirt is driven in axial rotation perpendicular to the contact surface, and the axial extraction or contact adhesion force when the skirt is withdrawn after a determinate period of contact.

10 Claims, 1 Drawing Sheet

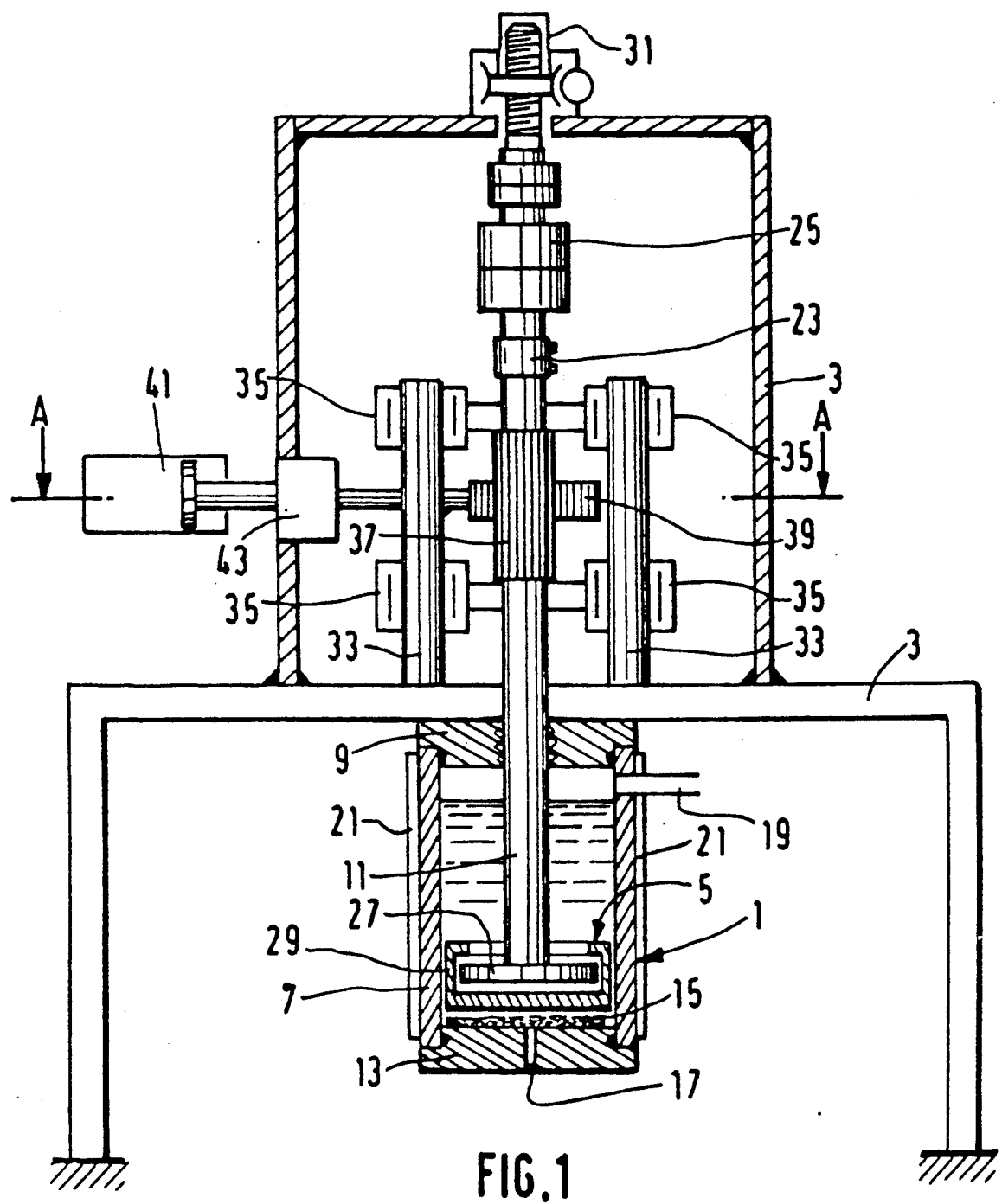
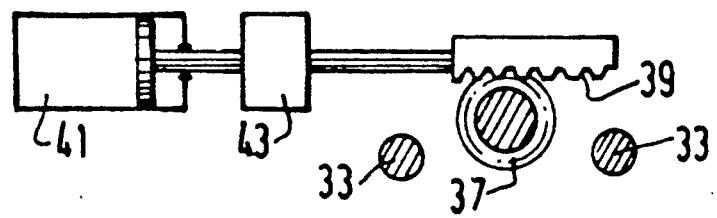
FIG.1
FIG.2

PROCEDURE AND CELL FOR MEASURING COEFFICIENTS OF ADHESION AND FRICTION OF A DRILLILNG FLUID

BACKGROUND OF THE INVENTION

This invention concerns a procedure and a measuring cell for drilling fluids which make it possible to determine the adhesion and friction characteristics of the fluid during drilling.

It is known that, during the drilling of a geothermal or mining oil well, the physical-chemical equilibrium of the drilling fluid, termed the "drilling mud," undergoes constant modification because of changes in its constituents. The various load products (bentonite. polymers, etc.) undergo continuous violent shearing processes, both at the pumps and at the turbines or ventilation holes of the tool to these shearing stresses are added rises in temperature and pressure. Furthermore, the imperative maintenance of a fluid density sufficient to counterbalance the pore pressure of the formations being drilled dictates, additionally, that the soil loads will increase the concentration of the solid materials content or that the addition of barium sulfate will be purposefully made. In this content, the characteristics of the drilling fluid change substantially as the drilling continues, with the result that the preponderant coefficients change at the point of contact between the drilling wall and the drilling tool fitting, including the coefficient of adhesion to the fitting, the moment of adhesion to the fitting the moment of friction on the fitting, etc. The poor control of these characteristics leads to a deterioration of drilling performance: for example, through the poor transmission of weight over the tool, especially as regards the drilling of deviated or horizontal wells, and through an increased moment which hinders the proper rotation of the fitting and of the tool. It also leads to jamming of the fitting and to problems in the walls especially in cases in which clayey soils are being drilled. Clayey formations or layers often give rise, moreover, to a sudden increase in pressure, which must be overcome during drilling. This pressure is called "abnormal pressure" and is due to the addition of the pressure arising from the weight of the layers of underlying sediments to the hydrostatic pore pressure.

SUMMARY OF THE INVENTION

One of the goals of the process and measuring cell according to the invention is to allow the clarification and optimization of the characteristics of drilling fluids by means of specific additives, in order to reduce or eliminate the many malfunctions linked to friction at a drilling operation, and in particular the jamming or binding of the fitting on the walls, a poor regulation of the weight on the tool, the over-sizing of the surface apparatuses because of the increased moment applied on tho fitting, etc.

Another goal of the process and measuring cell according to the invention is to anticipate the aforementioned problems at the drilling sites, by continuously undertaking representative and reliable measurements of the drilling fluids employed. To do this, the cell must be strong and of a reduced size to allow it to be placed in a control box at the drilling sites.

Thus, the measurement process according to the invention is characterized basically by the fact that, after the standardized filtering of the drilling fluid or mud, from which a solid phase called "filtration cake" and a liquid phase or filtrate collected on the downstream side of the filter are obtained, the process consists in placing a metal disk or movable piston in contact with the filtration cake in the presence of a contact pressure, and in measuring the moment of adhesion and friction when the disk or piston is driven in an axial rotational motion perpendicular to the contact surface, as well as the axial extraction or contact adhesion force, when the disk or piston is withdrawn after a determinate period of contact.

The adhesion and friction on the filtration cake may vary depending on the type of mud and on the additives, as well as on operating conditions such as pressure, temperature, contact surface geometry, etc. They make it possible, after analysis and interpretation, to optimize the drilling characteristics and to prevent all specifically related accidents, such as those previously mentioned.

It is possible to investigate the mechanics of the filtration in greater depth by measuring the penetration depth of the disk or piston as a function of time, contact pressure and temperature at the same time that conventional analytical data, such as filtrate volume, mud film, thickness of the filtration cake, etc., are being gathered.

Results may be analyzed interpreted and compared to the results of conventional soils-mechanics tests, in order to extend these friction and adhesion measurements as the basis for the formulation of a theory bearing on the mechanism at work.

The measurement cell used to implement the process according to the invention is characterized basically by the fact that it comprises a cylindrical chamber or housing containing, on its bottom, a standardized filter element for the filtration of the drilling fluids contained in the chamber, on which the solid phase or "filtration cake" is placed and beneath which the filtrate is drained and collected, the upper part of the chamber being crossed axially by the rod of a piston installed inside the device and whose T-shaped end or head receives a cylindrical skirt of approximately the same diameter as that of the housing and which can be driven by the stress provided by motor-driven means acting on the piston rod so as to produce, respectively, a rotational movement and an axial side-travel movement within the chamber, sensor elements for sensing the rotational moments and the side-travel forces being additionally connected to the motor-driven means.

In accordance with advantageous features of the invention, the chamber making up the measurement cell is mounted in such a way that it may be disassembled and forms a single piece with a frame bearing the motor-driven means for operating the piston. It comprises a cylindrical body, a bearing plate supporting the filter element which is radially grooved on the surface coming in contact with the filtering element and has a central hole to allow the flow and drainage of the collected filtrate and an upper support plate joined to the frame and through which the rod of the mobile piston passes while forming a fluid-tight seal.

The motor-driven means driving the piston in translational motion are advantageously composed of a lifting jack with side-travel guides operating by ball bearings and sliding on two parallel columns which are joined to the frame and which enclose the rod of the mobile piston.

The traction-compression force sensor used to measure contact adhesion is placed on the shaft connecting the piston with the lifting jack.

The rotation of the piston is ensured by means of a rack which meshes perpendicularly with a toothed-shaft or pinion portion of the piston rod, and its motion is activated by a dual-effect hydraulic jack.

The moment sensor is installed between the end of the rack and the hydraulic jack.

The contact pressure on the skirt of the mobile piston or on the disk results from the activation of the lifting jack and from the gas pressure within the chamber, such pressure allowing the filtration of the fluid from the upstream to the downstream side of the filter element.

BRIEF DESCRIPTION OF THE DRAWINGS

FIG. 1 is an axial cross-section of a measurement cell according to the invention, and FIG. 2 shows the rotational drive of the mobile piston along the line A—A in FIG. 1.

DETAILED DESCRIPTION OF THE PREFERRED EMBODIMENT

As shown in FIG. 1, the measurement cell according to the invention comprises a chamber 1 existing as a cylindrical housing joined to a bearing frame 3 and fitted with a mobile piston 5 on the inside. The chamber 1 comprises a cylindrical body 7 mounted on an upper plate 9 which is attached to the bearing frame and through which the rod 11 of the mobile piston passes, and a bearing plate 13 supporting a standardized filter element 15 (paper filter or porous metal disk) and grooved radially in an appropriate manner with a central hole 17 for drainage of the filtrate. A metal joint and a sealing ring ensure, in a conventional manner, the water-tightness on the circumference of the filter element and between the bearing plate and the cylindrical body. At the upper level, a flexible sealing ring and a double helical seal ensure the water-tightness, respectively, between the upper plate and the cylindrical body and at the point where the piston rod penetrates the upper plate. Assembly of the housing is achieved using three screws (not shown) positioned at 120° in the bearing plate.

A nitrogen gas feed 19 supplies the chamber at its upper part and pressurizes it to a value of 4 MPa.

Strip heaters 21 are mounted externally on the cylindrical body 7 of the chamber and raise its temperature to 150° C.

A water cooler 23 is, moreover, provided to reduce heat transfer by conduction on the piston rod to the traction-compression sensor 25.

The piston head 27 has a T-shaped section and the complementary skirt 29, a C-shaped section with a flat lower surface: its diameter is approximately the same as the diameter of the cylindrical body of the chamber. This skirt 29 forms one piece in translational motion, allowing for play, and in rotation (by hooking via roughened surfaces) with the piston head 27. The piston 5 is driven in an axial sliding motion (without producing friction on the cylindrical body) by a lifting jack 31 mounted to form one piece with the frame 3 at the upper end of the piston rod. The rod is guided axially by two columns 33 fastened to the frame and on which slide four ball-bearings 35 appropriately joined by twos on two levels to the piston rod 11. The length of the rod 37 extending between the two levels of bearings 35 has a circular toothed arrangement to form a pinion and meshes with a rack 39 driven perpendicularly in translational motion at its end and reversibly by a dual-effect hydraulic jack 41. The rack 39 is guided on a stationary slide (not shown) and moves from left to right and inversely, according to the movement of the jack. A first force sensor 43 for measuring the moment is inserted between the jack and the rack, while the second traction-compression sensor 25 is installed on the connecting shaft joining the mobile piston rod and the lifting jack.

In operation, after demounting the chamber from its upper support plate 9, the chamber is filled with drilling fluid or mud and is remounted and tightened by the three attachment screws fastened into the bearing plate. The chamber is then pressurized by the gas feed 19. Under the effect of the differential pressure on each side of the filter element 15, the drilling fluid begins to filter out, and the deposit left on top of the filter element constitutes the filtration cake. After a determinate filtration period, the lower flat surface of the skirt 29 is placed in contact with the cake by means of the piston 5 control. The contact between this surface and the cake is detected by the piston-rod force sensor 25. The force of the penetration of the skirt into the cake (compression) is read by the sensor. At this moment, and because the filtration cake insulates the bottom of the skirt, the piston skirt no longer exhibits equal pressure over its entire surface. The balance of forces (gas pressure) on the plate leads to a downward-directed vertical resultant which promotes the penetration of the skirt into the cake. The value of the penetration as a function of time can be measured.

After a determinate period of time, three types of parameters can be measured.

First, the wrenching force perpendicular to the contact surface of the skirt on the cake can be measured. The lifting jack 31 is used to raise the piston until contact is broken (detected by sensor 25) between the skirt and the cake. This traction value is read on the sensor and recorded. The maximum value is 2,000 daN, with an accuracy of 0.2%.

Second, the value of the turning contact-rupture moment or moment of adhesion can be measured. This procedure involves turning the rod 11 of the piston and, consequently, turning the skirt on the cake. This is effected by controlling the hydraulic jack 41 which drives the rack 39. The breaking of contact is detected by the sensor 43 at the end of the rack: this value is read and recorded by a linked electronic processing system equipped with a peak detector. The sensor possesses a 1,000 daN measuring range with an accuracy of 0.3%, which, given the 10 cm lever arm, gives a maximum amount of 100 daN.m.

Finally, the moment of friction can be measured. To do this, the hydraulic jack 41 is fed by a constant-capacity pump, thereby imparting to the skirt a constant angular speed of rotation. Thus, after measuring the preceding moment of adhesion, the moment of friction can be evaluated as a function of the speed of rotation.

This value makes it possible to better evaluate, in particular, the dynamic friction of the drilling fitting on the walls of the well, friction which increases the transmission force required and resists the progress of the tool.

It will be noted that the problems previously mentioned concerning abnormal pressures encountered in clayey layers or formations can also be more effectively mastered by using the invention. It is possible, in fact, to study the behavior of these clayey formations by conducting tests on compacted clay cakes of a predetermined nature (close to that which is presumed to exist at the drilling site), these cakes being, for example, contained in pellets having a diameter equal to that of the measuring chamber and which are placed on the bottom of the chamber where the filter is positioned, or above it. It is also possible to study the reactivity of these cakes of a determinate nature to various kinds of mud having given compositions, and to examine in particular their hydration. Further, it is possible to simulate the adhesion problems presented by these clays when they adhere to the drilling tools and gears (leading to jamming of the tools) by measuring the contact pressure of the disk on the cake (compaction pressure) at which the adherence of the clay to the disk is first perceived as the disk is being raised.

We claim:

1. A procedure for measuring characteristics of a drilling fluid, comprising the steps of: implementing a standardized filtration of a drilling fluid or mud sample to obtain a solid phase filtration cake and a liquid phase or filtrate collected on a downstream side of a filter, placing a metal disk in contact with a surface of the filtration cake under pressure, driving the disk in rotation and axial translation perpendicular to the contact surface, measuring the moments of adhesion and friction during said driving, withdrawing the disk after a predetermined period of contact, and measuring the axial extraction or contact adhesion force during said withdrawal, wherein the depth of penetration of the disk into the filtration cake is measured as a function of time, contact pressure, and temperature, at the same time as conventional analytical data are obtained concerning the filtrate volume, the mud-film, and the thickness of the filtration cake.

2. A measurement cell for measuring characteristics of a drilling fluid, comprising: a cylindrical housing, a standardized filter element disposed on a bottom of the housing for the filtration of drilling fluid inside the housing, on which a solid phase "filtration cake" is formed and beneath which a filtrate is drained and collected, a piston rod extending axially through an upper part of said housing, a T-shaped head fixed to an end of the rod within the housing, a cylindrical skirt of substantially the same diameter as that of the housing surrounding the piston rod head, motor-driven means for acting on the piston rod to produce a rotational motion and an axial translational motion within the housing, and sensor elements for sensing moments of rotation and axial travel forces, said sensor elements being linked to said motor-driven means, wherein the skirt has a C-shaped section and a flat lower surface whose diameter is approximately equal to the diameter of the cylindrical housing of the cell and forms one piece by hooking onto the piston rod head during rotation and slides axially without friction in the housing.

3. A measurement cell according to claim 2, wherein said housing is demountable and forms one piece with a frame supporting said motor-driven means.

4. A measurement cell according to claim 3, wherein said cell comprises a cylindrical body, a bearing plate supporting said filter element, grooved radially over a surface thereof in contact with the filter element, and having a central hole for the flow and drainage of the filtrate, and an upper support plate joined to the frame and through which the piston rod passes while forming a water-tight seal.

5. A measurement cell according to claim 4, wherein the motor-driven means comprises a lifting jack with side-travel guides including ball-bearings sliding on two parallel columns joined to the frame and flanking the piston rod.

6. A measurement cell according to claim 5, wherein a traction-compression force sensor for measuring contact adhesion is mounted on a shaft linking the piston rod with the lifting jack.

7. A measurement cell according to claim 6, wherein rotation of the piston rod is produced by a rack meshing perpendicularly with a toothed-shaft portion of the piston rod and driven in motion by a dual-effect hydraulic jack.

8. A measurement cell according to claim 7, wherein a moment sensor is installed between an end of the rack and the hydraulic jack.

9. A measurement cell according to claim 8, wherein the contact pressure on the skirt of the mobile piston results from the activation of the lifting jack and from gas pressure within the chamber, such pressure also implementing the filtration of the drilling fluid from an upstream to a downstream side of the filter element.

10. A procedure for measuring characteristics of a drilling fluid, comprising the steps of: implementing a standardized filtration of a drilling fluid or mud sample to obtain a solid phase filtration cake and a liquid phase or filtrate collected on a downstream side of a filter, placing a mobile piston in contact with a surface of the filtration cake under pressure, driving the piston in rotation and axial translation perpendicular to the contact surface, measuring the moments of adhesion and friction during said driving, withdrawing the piston after a predetermined period of contact, and measuring the axial extraction or contact adhesion force during said withdrawal, wherein the depth of penetration of the piston into the filtration cake is measured as a function of time, contact pressure, and temperature, at the same time as conventional analytical data are obtained concerning the filtrate volume, the mud-film, and the thickness of the filtration cake.

* * * * *